US005658586A

United States Patent [19]
Rajaiah et al.

[11] Patent Number: 5,658,586
[45] Date of Patent: Aug. 19, 1997

[54] DENTURE STABILIZING COMPOSITIONS

[75] Inventors: Jayanth Rajaiah, Loveland; David Alan Nichols; Kimberly Ann Gilday-Weber, both of Cincinnati, all of Ohio

[73] Assignee: The Procter & Gamble Company, Cincinnati, Ohio

[21] Appl. No.: 330,492

[22] Filed: Oct. 28, 1994

[51] Int. Cl.$^6$ .................................................. A61F 13/56
[52] U.S. Cl. .......................... 424/435; 428/40.1; 428/343; 428/355 EN; 523/120
[58] Field of Search .............................. 424/435; 428/40, 428/286, 290, 343, 355; 523/120

[56] References Cited

U.S. PATENT DOCUMENTS

| | | | |
|---|---|---|---|
| 2,897,593 | 8/1959 | Hollander et al. | 32/2 |
| 3,575,915 | 4/1971 | Novak et al. | 260/29.6 |
| 4,202,098 | 5/1980 | Russo | 433/168 |
| 4,373,036 | 2/1983 | Chang et al. | 523/120 |
| 4,503,116 | 3/1985 | Lapidus | 428/286 |
| 4,529,748 | 7/1985 | Wienecke | 523/120 |
| 4,632,880 | 12/1986 | Lapidus | 428/523 |
| 4,758,630 | 7/1988 | Shah et al. | 525/207 |
| 4,772,470 | 9/1988 | Inoue et al. | 424/435 |
| 4,880,702 | 11/1989 | Homan et al. | 428/354 |
| 5,073,604 | 12/1991 | Holeva et al. | 525/327.8 |
| 5,158,825 | 10/1992 | Altwirth | 428/286 |
| 5,166,233 | 11/1992 | Kuroya et al. | 524/37 |
| 5,204,414 | 4/1993 | Pelah et al. | 525/327.8 |
| 5,209,777 | 5/1993 | Altwirth | 106/35 |
| 5,369,145 | 11/1994 | Gasman et al. | 523/120 |
| 5,525,652 | 6/1996 | Clarke et al. | 524/37 |

FOREIGN PATENT DOCUMENTS

| | | |
|---|---|---|
| 0353375 | 2/1990 | European Pat. Off. . |
| 555 019 A1 | 8/1993 | European Pat. Off. . |
| 3613432 | 10/1987 | Germany . |
| 63-54318 | 3/1988 | Japan . |
| 4-149110 | 5/1992 | Japan . |
| 5-65211 | 3/1993 | Japan . |
| 5-65210 | 3/1993 | Japan . |
| WO96/04883 | 2/1996 | WIPO . |

OTHER PUBLICATIONS

U.S. application No. 08/330,470, Rajaiah et al., filed Oct. 28, 1994.

*Primary Examiner*—James J. Seidleck
*Assistant Examiner*—Michael A. Williamson
*Attorney, Agent, or Firm*—Mary Catherine Poland; Douglas C. Mohl; Jacobus C. Rasser

[57] ABSTRACT

The subject invention encompasses a denture adhesive composition comprising one or more adhesive components suitable for adhering to the oral cavity and a denture base and at least one non-adhesive self-supporting layer wherein the self-supporting layer is selected from the group consisting of polyester, polypropylene, nylon, rayon, polyethylene oxide, cellulose acetate, cellulose derivatives, cloth, paper, microcrystalline wax, synthetic fibers, natural fibers, and mixtures thereof.

14 Claims, No Drawings

DENTURE STABILIZING COMPOSITIONS

BACKGROUND OF THE INVENTION

Ordinary removable dentures, dental plates and the like, comprise teeth mounted in a suitable plate or base. Although dentures generally are skillfully prepared, often they do not fit perfectly. Moreover, no matter how satisfactory at first, after a period of time the fit of the denture becomes loose and imperfect due to natural shrinkage and changes in the gums, underlying bone structure, mucous tissues, and the like. Loose and imperfectly fitted dentures can be corrected and stabilized by the use of a denture stabilizer. Denture stabilizers are used to fill the interstices between the dentures and the gums or tissues. Prior to placement of the denture in the oral cavity, a denture stabilizer is applied to the denture-plate surface which, for a perfect fit, should uniformly contact the gums and mucous tissues. The denture stabilizer is formulated not only for its adherent properties, but also to provide a cushion or gasket between the denture and the gums or tissues, thereby positioning the denture securely in the oral cavity.

Several deficiencies commonly exist with denture stabilizing or adhesive compositions. Common aesthetic deficiencies include oozing of the adhesive from under the dental plate during insertion and throughout the wearing period and messiness and difficulty of removing the residual adhesive from the mouth and dentures. Additionally, food may become trapped between the denture and the oral cavity of the wearer.

Considerable effort has been made over the years to develop improved denture adhesive compositions. Both synthetic and natural polymers and gums have been used singly, in combination, and in combination with various adhesives in an attempt to lessen the deficiencies noted above.

U.S. Pat. No. 4,880,702 to Homan et al., issued Nov. 14, 1989 discloses a denture stabilizer in the form of a strip consisting of three layers. The two outside layers consist of a polymer selected from the group consisting of polyethylene oxide having an average molecular weight of about 200,000 to 10,000,000, sodium carboxymethylcellulose, polyvinyl alcohol, and mixtures thereof. The inside layer consists of microcrystalline wax and a polymer sufficient to adhere the inside layer to gums and a denture base, after contact with water, when the outside layers have been dissolved. European Patent Application 0,353,375 to Altwirth published Feb. 7, 1990, discloses an adhesive insert for dentures consisting of a adhesive permeated fibrous fleece and an adhesive consisting of a pasty mixture of alginate and/or carboxymethylcellulose, polyvinyl acetate and an alcoholic solvent. Despite the above-noted technologies as well as many others, need still exists for improved denture stabilizing compositions which offer a secure hold and are aesthetically pleasing to the user and which ooze less than currently available products.

It has been discovered, in accordance with the present invention, that a denture adhesive composition can be formulated having excellent adhesive quality. These adhesive compositions effectively stabilize dentures while oozing less and providing pleasing aesthetics to the user. The invention denture adhesive compositions may also be effectively used as a wound dressing, underwater adhesive, bioadhesive, and/or as a delivery vehicle for other actives.

It is an object of the present invention to provide a denture adhesive composition which effectively holds dentures in place for a prolonged period of time yet allows for easy removal of the denture on demand. It is also an object of the invention to provide an improved adhesive composition which may be used with dentures and which oozes less during insertion and wear than currently available stabilizers and is aesthetically pleasing to the user.

These and other objects of the present invention will become readily apparent from the detailed description which follows.

SUMMARY OF THE INVENTION

The present invention relates to a denture adhesive composition comprising one or more adhesive components suitable for adhering to the oral cavity and a denture base and at least one non-adhesive self-supporting layer wherein the non-adhesive self-supporting layer is selected from the group consisting of polyester, polypropylene, nylon, rayon, polyethylene oxide, cellulose acetate, cellulose derivatives, cloth, paper, microcrystalline wax, synthetic fibers, natural fibers, and mixtures thereof.

DETAILED DESCRIPTION OF THE INVENTION

The denture adhesive compositions of the present invention comprise one or more adhesive components and at least one non-adhesive self-supporting layer. Preferably, the present compositions comprise at least two adhesive components wherein one of the adhesive components is carboxymethylcellulose, sodium alginate, polyethylene oxide, karaya gum, and mixtures thereof.

The present denture adhesive compositions are thoroughly moistened and applied to dentures. The attachment of the adhesive component to the non-adhesive self-supporting layer provides a composition which may ooze less in the oral cavity than conventional adhesive creams which contain oily carrier vehicles. This attachment also provides a composition which is easy to clean from dentures since the non-adhesive self-supporting layer maintains its strength and integrity in the presence of water and/or saliva, and allows the composition to be peeled from the dentures upon their removal. A detailed description of essential and optional components of the present invention is given below.

Non-Adhesive Self-Supporting Layer

The present denture adhesive compositions comprise at least one non-adhesive self-supporting layer. The non-adhesive self-supporting layer is characterized by its ability to maintain strength and provide integrity for the adhesive composition in the presence of water and/or saliva. The non-adhesive self-supporting layer may include such materials as polyester, polypropylene, nylon, rayon, polyethylene oxide, cellulose acetate, cellulose derivatives, cloth, paper, microcrystalline wax, synthetic fibers, natural fibers, and mixtures thereof. Preferred are cellulose derivatives, polyester, polypropylene, nylon, rayon, cloth, paper, microcrystalline wax, and mixtures thereof. Most preferred are polyester, polypropylene, rayon, nylon, cloth and paper.

The non-adhesive self-supporting layer may be in any physical form suitable for providing strength and/or integrity to the present adhesive compositions. Such physical forms include non-woven, woven, continuous, chopped, and combinations thereof. In addition, the non-adhesive self-supporting layer may be formed by any process commonly known in the art. Such processes include un-bonded, spraybonded, spun-bonded, needle-punched, carded, thermal bonded hydroentangled, meltblown, aperture print bonded, needled, wet-laid, dry-laid, and combinations thereof.

Adhesive Components

The present invention compositions comprise one or more adhesive components suitable for adhering to the oral cavity and a denture base. These adhesive components are used in safe and adhesively effective amounts. The term "safe and adhesively effective amount" as used herein means an amount sufficient to provide adherence to the oral cavity. In the present denture adhesive compositions, polyvinyl acetate is not included as a suitable "other adhesive component".

Suitable adhesive components include a water-soluble hydrophilic colloid or polymer having the property of swelling upon exposure to moisture to form a mucilaginous mass. Such adhesive materials include natural gums, synthetic polymeric gums, adhesive materials commonly employed in denture stabilizing compositions, synthetic polymers, mucoadhesive polymers, hydrophilic polymers, saccharide derivatives, cellulose derivatives, and mixtures thereof. Examples of such materials include karaya gum, guar gum, gelatin, algin, sodium alginate, tragacanth, chitosan, polyethylene glycol, acrylamide polymers, carbopol, polyvinyl alcohol, polyamines, polyquarternary compounds, polybutenes, silicones, ethylene oxide polymers, polyvinylpyrrolidone, cationic polyacrylamide polymers.

Preferred are cellulose derivatives such as methylcellulose, sodium carboxymethylcellulose, hydroxyethylcellulose, hydroxypropylcellulose, hydroxypropylmethylcellulose, carboxymethylcellulose. Most preferred are carboxymethylcellulose, polyethylene glycol, polyethylene oxide, karaya gum, sodium alginate, chitosan, polyvinyl alcohol, and mixtures thereof. In general, the other adhesive components may be present at a level of from about 10% to about 98%, preferably from about 20% to about 95%, and most preferably from about 40% to about 95%, by weight of the composition.

Other Ingredients

One or more toxicologically-acceptable plasticizers may also be included in the present compositions. The term "toxicologically-acceptable", as used herein, is used to describe materials that are suitable in their toxicity profile for administration to humans and/or lower animals. Plasticizers that may be used in the present compositions include dimethyl phthalate, diethyl phthalate, dioctyl phthalate, glycerin, diethylene glycol, triethylene glycol, Igepal, Gafac, sorbitol, tricresyl phosphate, dimethyl sebacate, ethyl glycolate, ethylphthalyl ethyl glycolate, o- and p-toluene ethyl sulfonamide, and mixtures thereof. Plasticizers may be present at a level of from about 0% to about 70%, preferably from about 1% to about 30%, by weight of the compositions.

The denture adhesive compositions may be used as denture adhesives or bioadhesives and comprise one or more therapeutic actives suitable for mucosal or topical administration. The phrase "suitable for mucosal or topical administration", as used herein, describes agents which are pharmacologically active when absorbed through internal mucosal surfaces of the body such as the oral cavity, or applied to the surfaces of the skin. Therapeutic actives may be present at a level of from about 0% to about 70%, by weight of the composition.

Therapeutic actives that are useful in these compositions include antimicrobial agents such as iodine, sulfonamides, bisbiguanides, or phenolics; antibiotics such as tetracycline, neomycin, kanamycin, metronidazole, or clindamycin; anti-inflammatory agents such as aspirin, acetaminophen, naproxen and its salts, ibuprofen, ketorolac, flurbiprofen, indomethacin, eugenol, or hydrocortisone; dentinal desensitizing agents such as potassium nitrate, strontium chloride or sodium fluoride; anesthetic agents such as lidocaine or benzocaine; anti-fungals; aromatics such as camphor, eucalyptus oil, and aldehyde derivatives such as benzaldehyde; insulin; steroids; and anti-neoplastics. It is recognized that in certain forms of therapy, combinations of these agents in the same delivery system may be useful in order to obtain an optimal effect. Thus, for example, an antimicrobial and an anti-inflammatory agent may be combined in a single delivery system to provide combined effectiveness.

Other suitable ingredients include colorants, preservatives such as methyl and propyl parabens; thickeners such as silicon dioxide, and polyethylene glycol; and vehicles such as liquid petrolatum, petrolatum, mineral oil and glycerin. Colorants, preservatives, thickeners and vehicles may be present at levels of from about 0% to about 20%, by weight of the composition.

The present denture adhesive compositions may also comprise a coating which is sticky to dry dentures and, if present, will be placed on one side of the denture adhesive composition. Compositions suitable for use as this coating include polybutenes, silicones, rubbers, petrolatum, natural polymers, synthetic polymers, and mixtures thereof. The adhesive layer may be present at a level of from about 0% to about 70%, and preferably from about 0.5% to about 20%, by weight of the composition.

The compositions of the present invention may also include one or more components which provide flavor, flagrance, and/or sensate benefit. Suitable components include natural or artificial sweetening agents, menthol, menthyl lactate, wintergreen oil, peppermint oil, spearmint oil, leaf alcohol, as well as coolants 3-1-menthoxypropane-1,2-diol and paramenthane carboxyamide agents such as N-ethyl-p-menthane-3-carboxamide which is described in U.S. Pat. No. 4,136,163 to Watson et. al., which is incorporated by reference herein in its entirety. These agents may be present at a level of from about 0% to about 50%, by weight of the composition.

Process for Preparation of the Composition

A process for the preparation of the present denture adhesive compositions comprises coating a weighed amount of the adhesive components onto the non-adhesive serf-supporting layer using water as a process aid. The adhesive components may be coated on the non-adhesive self-supporting layer using various methods. These include: wetting the non-adhesive self-supporting layer with water, uniformly sifting the adhesive powder onto the wet layer and then rewetting the layer with water; dissolving the adhesive component in water and coating the resulting solution onto the layer; coating the layer with the slurry produced during Gantrez® processing; and incorporating the adhesive component into the layer as the layer is being formed.

The layer is then dried. Next, the denture adhesive composition is mechanically softened by running it through a ring-roller or micro-cracker or any other suitable means. The composition is then pressed smooth in a hydraulic press or flat-roller or other suitable means. The composition is then die-cut into denture shapes. These shapes may facilitate application of the composition to the dentures.

The following examples further describe and demonstrate embodiments within the scope of the present invention. The examples are given solely for the purpose of illustration and are not to be construed as limitations of the present invention, as many variations thereof are possible without departing from the spirit and scope of the invention.

EXAMPLES I-V

| Example # | Adhesive Component | Non-Adhesive Self-Supporting Layer |
|---|---|---|
| I | Carboxymethylcellulose | non-woven polyester |
| II | Karaya Gum | non-woven polyester |
| III | Sodium Alginate | non-woven polypropylene |
| IV | Poly Ethylene Oxide | cloth |
| V | Poly Ethylene Glycol | paper |

Examples I-V are prepared as follows. Wet 58" by 20" of the non-adhesive self-supporting layer with water. Uniformly coat 150 grams of the adhesive component onto the layer and rewet the layer with water. Dry the layer. Mechanically soften the denture adhesive composition by ring-roller, and then smooth the composition on a hydraulic press. Cut the composition into denture-shaped wafers. Thoroughly moisten the wafers and apply to the dentures. This wafer is peelable from the denture and forms a sticky seal that holds the dentures in place, does not ooze, and aids in preventing food from sticking between the dentures and gums.

What is claimed is:

1. A dry denture adhesive composition comprising:
   a) one or more adhesive components, excluding polyvinyl acetate, suitable for adhering to an oral cavity and a denture base, wherein the adhesive components are water soluble; and
   b) at least one non-adhesive self-supporting layer wherein the self-supporting layer is selected from the group consisting of polyester, polypropylene, nylon, rayon, polyethylene oxide, cellulose acetate, cellulose derivatives, cloth, paper, microcrystalline wax, synthetic fibers, natural fibers, and mixtures thereof;
   and wherein the denture adhesive composition, after being thoroughly moistened is applied to the denture base and forms a sticky seal between the oral cavity and the denture base.

2. The denture adhesive composition according to claim 1 wherein the non-adhesive self-supporting layer is in a physical form selected from the group consisting of non-woven, woven, continuous, chopped, and combinations thereof.

3. The denture adhesive composition according to claim 1 wherein the non-adhesive self-supporting layer is formed by a process selected from the group consisting of un-bonded, spraybonded, spun-bonded, needle-punched, carded, thermal bonded hydroentangled, meltblown, aperture print bonded, needled, wet-laid, dry-laid, and combinations thereof.

4. The denture adhesive composition according to claim 1 wherein one of the adhesive components is a polymeric material selected from the group consisting of natural gums, synthetic polymers, mucoadhesive polymers, hydrophilic polymers, natural polymers, saccharide derivatives, cellulose derivatives, and mixtures thereof.

5. The denture adhesive composition according to claim 4 wherein one or more of the adhesive components is selected from the group consisting of hydroxyethylcellulose, hydroxypropylcellulose, hydroxypropylmethylcellulose, carboxymethylcellulose, polyethylene glycol, polyethylene oxide, karaya gum, sodium alginate, chitosan, guar gum, polyacrylic acid, carbopol, polyvinyl alcohol, polyamines, polyquarternary compounds, polybutenes, silicones, cellulose derivatives, and mixtures thereof.

6. The denture adhesive composition according to claim 1 further comprising a toxicologically-acceptable plasticizer.

7. The denture adhesive composition according to claim 6 wherein the plasticizer selected from the group consisting of dimethyl phthalate, diethyl phthalate, dioctyl phthalate, glycerin, diethylene glycol, triethylene glycol, Igepal, Gafac, sorbitol, tricresyl phosphate, dimethyl sebacate, ethyl glycolate, ethylphthalyl ethyl glycolate, o- and p-toluene ethyl sulfonamide, and mixtures thereof.

8. The denture adhesive composition according to claim 1 further comprising one or more components selected from the group consisting of flavors, fragrances, sensates, and mixtures thereof.

9. The denture adhesive composition according to claim 8 wherein the flavors, fragrances, and sensates are selected from the group consisting of menthol, menthyl lactate, peppermint oil, spearmint oil, leaf alcohol, paramenthane caboxyamides, and mixtures thereof.

10. The denture adhesive composition according to claim 1 used as a denture adhesive or a bioadhesive and further comprising one or more therapeutic actives suitable for mucosal or topical administration.

11. The denture adhesive or bioadhesive according to claim 10 wherein the therapeutic actives are selected from the group consisting of anethestic, analgesic, antibiotic, anti-inflammatory, antibacterial, antimicrobial, antifungal, antihistamine, insulin, steroid, and antineoplastic agents.

12. The denture adhesive composition according to claim 1 further comprising a coating that is sticky to dry dentures wherein the coating is coated on one side of the denture adhesive composition.

13. The denture adhesive composition according to claim 12 wherein the coating is selected from the group consisting of polybutenes, silicones, rubbers, petrolatum, natural polymers, synthetic polymers, and mixtures thereof.

14. A process for the preparation of the denture adhesive composition according to claim 1 wherein the composition is mechanically softened, pressed smooth and cut into denture shapes.

* * * * *